US012655459B2

(12) United States Patent
Tyo et al.

(10) Patent No.: US 12,655,459 B2
(45) Date of Patent: Jun. 16, 2026

(54) DETECTION OF ANALYTE

(71) Applicant: Northwestern University, Evanston, IL (US)

(72) Inventors: Keith E.J. Tyo, Evanston, IL (US); Catherine Elizabeth Majors, Evanston, IL (US)

(73) Assignee: Northwestern University, Evanston, IL (US)

( * ) Notice: Subject to any disclaimer, the term of this patent is extended or adjusted under 35 U.S.C. 154(b) by 878 days.

(21) Appl. No.: 17/877,679

(22) Filed: Jul. 29, 2022

(65) Prior Publication Data

US 2023/0035412 A1 Feb. 2, 2023

Related U.S. Application Data

(60) Provisional application No. 63/228,002, filed on Jul. 30, 2021.

(51) Int. Cl.
| | |
|---|---|
| *C12Q 1/00* | (2006.01) |
| *C12Q 1/527* | (2006.01) |
| *C12Q 1/533* | (2006.01) |
| *G01N 21/64* | (2006.01) |

(52) U.S. Cl.
CPC ............. *C12Q 1/004* (2013.01); *C12Q 1/527* (2013.01); *C12Q 1/533* (2013.01); *G01N 21/6428* (2013.01); *G01N 2021/6439* (2013.01)

(58) Field of Classification Search
None
See application file for complete search history.

(56) References Cited

U.S. PATENT DOCUMENTS 11,774,453 B2 10/2023 Dixon et al.

OTHER PUBLICATIONS

Karimova et al. A bacterial two-hybrid system that exploits a cAMP signaling cascade in *Escherichia coli*. Methods Enzymol. 2000;328:59-73. (Year: 2000).*
Ladant et al. Genetic systems for analyzing protein-protein interactions in bacteria. Res Microbiol. Nov. 2000;151(9):711-20. (Year: 2000).*
Banaszynski et al. Characterization of the FKBP.rapamycin.FRB ternary complex. J Am Chem Soc. Apr. 6, 2005;127(13):4715-21. (Year: 2005).*
Cameron et al. CRP binding and transcription activation at CRP-S sites. J Mol Biol. Nov. 7, 2008;383(2):313-23 (Year: 2008).*

(Continued)

*Primary Examiner* — Rebecca M Giere
*Assistant Examiner* — Alexander Alexandrovic Volkov
(74) *Attorney, Agent, or Firm* — Foley & Lardner LLP

(57) ABSTRACT

A method for detecting an analyte is described in which the simultaneously binding of two fusion proteins (i.e., a sandwich assay in solution) is used, bringing two halves of a split enzyme together to produce product, which is detected via a FRET-based biosensor. The method may incorporate an autocatalytic feedback loop that responds to enzymatic product by producing more product to provide ultrasensitive, bistable detection of analyte that is tunable over several orders of magnitude. This system is broadly applicable for protein and small molecule detection.

18 Claims, 4 Drawing Sheets

(56)     References Cited

OTHER PUBLICATIONS

Chaurasia et al. Molecular insights into the stabilization of protein-protein interactions with small molecule: The FKBP12-rapamycin—FRB case study, Chemical Physics Letters, vol. 587, 2013, pp. 68-74 (Year: 2013).*

Mukherjee et al. A novel biosensor to study cAMP dynamics in cilia and flagella. Elife. Mar. 22, 2016;5:e14052. (Year: 2016).*

Gruteser et al. Establishing a sensitive fluorescence-based quantification method for cyclic nucleotides. BMC Biotechnol. Aug. 27, 2020;20(1):47. (Year: 2020).*

* cited by examiner

DETECTION OF ANALYTE

The present application claims priority to U.S. Provisional Patent Application No. 63/228,002 filed Jul. 30, 2021, which is incorporated herein by reference in its entirety.

The present disclosure relates to methods for detecting an analyte using split enzyme constructs as detection arms to form a complex with the analyte or which utilize fusions of split enzymes with receptor protein to create an autocatalytic feedback loop.

BACKGROUND

Rapid, inexpensive detection of biomarkers at the point of care is vital for many clinical purposes. However, limitations in current detection platforms have prevented the sensitive detection of many protein and small molecule biomarkers, forcing clinicians to rely on either potentially inaccurate empirical diagnosis or expensive lab tests to make critical treatment decisions. Sensitive detection of nucleic acid targets has been readily achieved by exploiting Watson-Crick base pairing to amplify signals (PCR, LAMP, Cas9, etc.), but there has been a lack of innovation for detection of low concentration antigens and small molecules at the point of care.

Biology has evolved intricate mechanisms for rapidly amplifying protein signals in vivo via post-translational modification and protein based signaling networks. Towards the goal of developing novel, rapid, ultrasensitive diagnostics, protein-based signaling networks incorporating self-amplifying enzymatic pathways can be used to provide biomarker detection platforms with unparalleled sensing capabilities. In particular, two mechanisms of protein signaling networks with potential for diagnostics have been found to be useful: split enzyme reconstitution and autocatalytic positive feedback loops. In particular, in vitro use of split adenylate cyclase is demonstrated for small molecule detection. Detection of the analyte can be accomplished by the simultaneously binding of two proteins (i.e., a sandwich assay in solution), bringing two halves of adenylate cyclase together and producing cAMP. Second, fusions of split adenylate cyclase and cAMP receptor protein to create an autocatalytic feedback loop in vitro were investigated. This loop responded to cAMP by producing more cAMP. Finally, ordinary differential equation-based models can be applied to understand and engineer diagnostic properties. Dynamic models of these protein-signaling networks are established by measured experimental parameters. These models can create a combined model for a high sensitivity, fast small molecule sensor. The methods are broadly applicable for protein and small molecule detection and could be used to detect a wide range of target analytes with known antibody binding domains.

An objective is to provide a platform for the detection of many protein and small molecule analytes currently unable to be rapidly detected at the point of care.

SUMMARY

An embodiment is a method of detecting an analyte comprising adding to a sample comprising adenosine triphosphate and an unknown concentration of an analyte detection reagents comprising a first reagent and a second reagent, the first reagent comprising a first fusion protein bound to a first fragment of a first cAMP catalyzing enzyme the second reagent comprising a second fusion protein bound to a second fragment of the first cAMP catalyzing enzyme, wherein the first fusion protein and the second fusion protein are configured to form with the analyte a protein-analyte-protein complex, wherein the first fragment of the first cAMP catalyzing enzyme and the second fragment of the first cAMP catalyzing enzyme when complexed as a protein-analyte-protein complex perform a function of the cAMP catalyzing enzyme; and measuring a cAMP concentration in the sample and determining a concentration of the analyte based on the measured cAMP concentration.

Another embodiment is a kit for determining a concentration of an analyte, comprising a first reagent comprises a first fusion protein bound to a first fragment of a first cAMP catalyzing enzyme; and a second reagent comprises a second fusion protein bound to a second fragment of the first cAMP catalyzing enzyme, the first fusion protein and the second fusion protein are configured to form with the analyte a protein-analyte-protein complex, the first fragment of the first cAMP catalyzing enzyme and the second fragment of the first cAMP catalyzing enzyme together restitute the full first cAMP catalyzing enzyme.

BRIEF DESCRIPTION OF THE FIGURES

FIG. 1A-C provide an overview of an embodiment of the detection method. (A) In the presence of rapamycin, the FKBP12-rapamycin-FRB protein complex will form, reconstituting the T25 and T18 split adenylate cyclase fragments fused to the binding domains; this will result in an accumulation of cAMP. (B) The cAMP molecules will then be free to associate with CRP molecules fused to split adenylate cyclase halves; the CRP-cAMP compounds will bind to DNA fragments with multiple CRP promotor sequences, thereby reconstituting additional adenylate cyclase and creating a feed-forward loop. (C) The increase of cAMP molecules will be detected using a cAMP biosensor in which a FRET-based fluorescence shift occurs upon binding.

DETAILED DESCRIPTION

Figure 2:
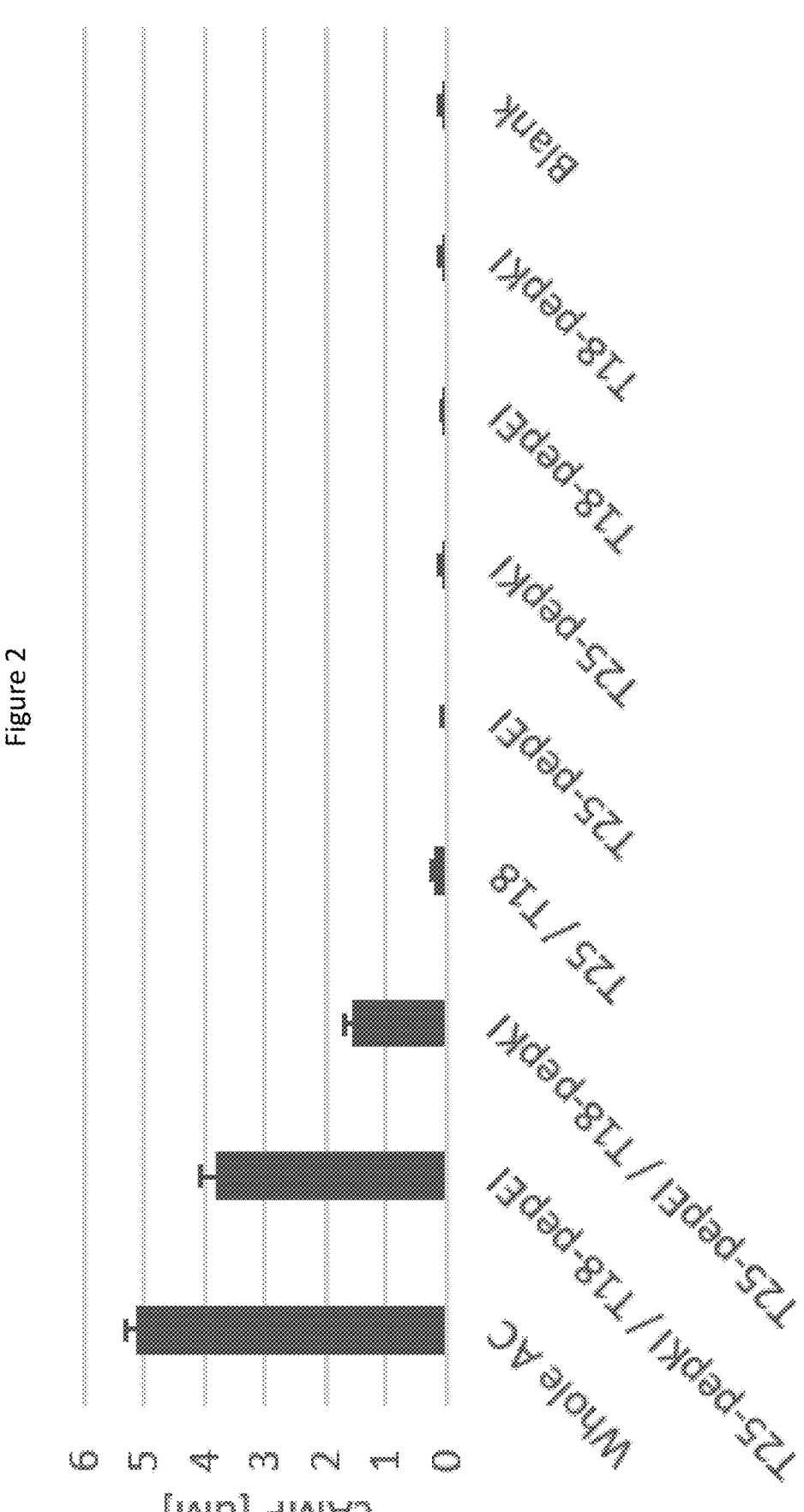
FIG. 2 shows relative activities of different adenylate cyclase constructs. cAMP accumulation of positive and negative control fragments showing comparable activity of positive control reactions (T25-pepKI/T18-pepEI and T25-pepKI/T18-pepEI) with whole adenylate cyclase and limited activity in the negative control (T25/T18). Positive control proteins are composed of the split fragments of adenylate cyclase (T25 and T18) fused to self-assembling leucine zipper coiled-coils (pepKI and pepEI). Negative control proteins are composed of the split fragments of adenylate cyclase (T25 and T18) with no binding/assembly domains. All reactions were run in triplicate at 37° C. for 30 minutes with 100 nM of each adenylate cyclase fragment and 100 μM ATP in a 25 mM Tris 150 mM NaCl reaction buffer before being measured using a cAMP ELISA.

The present invention is described herein using several definitions, as set forth below and throughout the application.

Unless otherwise specified or indicated by context, the terms "a", "an", and "the" mean "one or more."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus 10% of the particular term and "substantially" and "significantly" will mean plus or minus>10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be inter-preted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel char-acteristics of the claim.

Although the present disclosure uses adenylate cyclase as an enzyme, which may be split into a first fragment and a second fragment, other enzymes, such as luciferase and β-galactosidase, may be also used.

Although the present disclosure uses FKBP-12 and FRB as protein domains to sense rapamycin as an exemplary analyte, other sensing domains may be used for detecting other analytes, which may be clinically relevant analytes, i.e. analytes, which may be use for determining whether or not a subject, such as a human being, has a condition, such as a disease.

The present disclosure may allow detection of low con-centration of analytes, such as from 100 pM to 500 nM or from 200 pM to 200 nM or from 500 pM to 100 nM or from 500 pM to 50 nM or from 500 pM to 10 nM, the present technology may also allow detection of higher concentra-tions of analytes as well.

EXAMPLES

The following Examples are illustrative and should not be interpreted to limit the scope of the claimed subject matter.

An Enzyme Self-Amplification System for Ultrasensitive Detection of Biomarkers at the Point of Care Research Training Plan Significance Rapid, inexpensive detection of biomarkers at the point of care (POC) is vital for many clinical purposes. For analytes where POC testing is possible, improved disease screening, diagnosis, monitoring, and management have been achieved. A common POC test uses paper-based lateral flow assays (LFAs) where results can be read out in under 15 minutes. While these tests have been very effective in some applications, the lack of signal amplification has limited the use of LFAs for detecting analytes present at low concen-trations in patient samples, such as viral antigens.[1,2]

Most LFAs rely on sandwich binding of the analyte between two antibodies, one on a paper strip and another conjugated to a color change particle. Antibodies and other affinity reagents can be engineered to enable picomolar affinity for antigens.[16,17] Recent advancements in nanobody generation have demonstrated binding affinities in the fem-tomolar range.[18] Despite this affinity, POC diagnostics (like LFAs) achieve 100-fold worse sensitivities on the order of 10 nM.[19] This is because, currently, there is no way to translate the sandwich binding events into a detectable readout when the binding events are at picomolar concen-trations.

Another mode of disease detection, nucleic acid amplifi-cation tests (NAATs), overcomes this limitation of lateral flow assays. Because NAATs can use Watson-Crick base pairing to readily amplify signals (PCR, LAMP, Cas9, etc.), highly precise and very sensitive assays are possible. While nucleic acid analytes have powerful assays for detection, there has been a lack of innovation for detection of low concentration antigens and small molecules at the POC where base-pairing amplification cannot be used. However, biology has evolved intricate mechanisms for rapidly ampli-fying protein signals in vivo via post-translational modifi-cation and protein based signaling networks. Here, the inventors propose a detection scheme that uses a self-amplifying enzymatic pathway, amplifying a signal like that seen in PCR while resulting in readouts in less than a minute. The contributions of the present disclosure may be signifi-cant because it would be the first demonstration of a self-amplifying antigen detection system that could be used as a platform for diagnostics at the POC.

Proposed Technology Overview

Figure 1A:
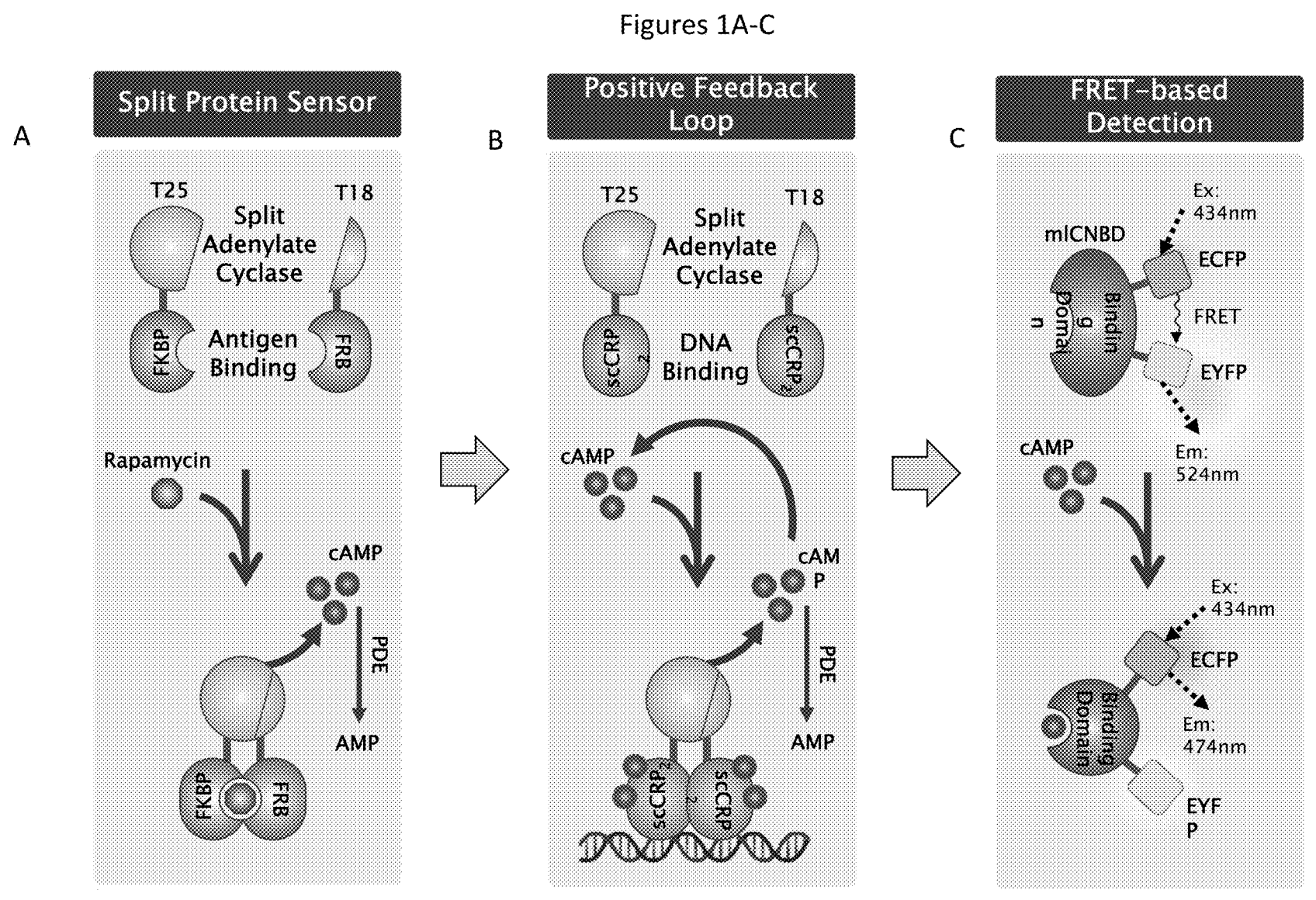

The proposed detection platform builds on the well-characterized practice of using split protein systems for detecting protein-protein interactions. Traditionally, these systems have been used to investigate whether two proteins directly interact in vivo; the inventors propose to use split adenylate cyclase to detect the presence of an analyte of interest in vitro via mediated interactions of the two com-ponent halves with the analyte of interest (i.e., a sandwich assay, FIG. 1A). Adenylate cyclase catalyzes rapid synthesis of cAMP,[20] and the inventors propose to use the initial generation of cAMP from the analyte mediated reconstitution of adenylate cyclase to drive a self-amplifying positive feedback loop (FIG. 1B). In some embodiments, the feedback loop may be composed of split adenylate cyclase fused to cAMP binding protein (CRP, also known as catabolite binding protein) and small DNA fragments that act as scaffolds. CRP cooperatively binds two cAMP molecules; in native systems when a CRP-cAMP compound forms, it binds to DNA promoter regions to drive transcription/translation. In order to drive all outputs by rapid protein interactions alone, in the system multiple CRP-cAMP complexes will bind to short, scaffold DNA fragments that contain multiple repeats of the promotor region sequence for CRP.[14] Because CRP may be fused with split adenylate cyclase halves, upon binding to the scaffold DNA fragments, additional adenylate cyclase will be reconstituted and drive increased production of cAMP, which in turn will further reconstitute adenylate cyclase fused with CRP. This autocatalytic cycle may exponentially continue until the system is saturated and all CRP-adenylate cyclase fusions are bound to scaffold DNA and activated. The activation of the system can be tuned with the inclusion of phosphodiesterase (PDE). PDE degrades cAMP to inactive AMP,[21] which does not bind to and activate CRP. By incorporating various concentrations of PDE, minor fluctuations in cAMP concentration due to random, stochastic interactions of split adenylate cyclase can be negated; further the system will only by triggered when cAMP generation reliably exceeds that of degradation by PDE, allowing the system to be tuned to trigger only once a clinically relevant target analyte concentration is present. cAMP accumulation will be detected via a FRET-based cAMP biosensor that has been previously demonstrated in vitro[8,10] (FIG. 1C). Upon cAMP binding to the biosensor, a conformational change in the binding domain (Epac1 shown in FIG. 1C) causes the fused fluorescent domains (ECFP as FRET donor and EYFP as FRET acceptor) to move farther apart, resulting in decreased FRET and a shift in the fluorescence emission wavelength.

An initial ODE-based model of the proposed platform has been created using available kinetic parameters of PDE and in vivo expression of split adenylate cyclase reported in literature.[11,22-25] Simulations demonstrated tunable ON/OFF behavior across a range of the analyte rapamycin concentrations by tuning PDE concentration. Importantly, the modeled system also showed bistability; once the system is activated at the "trigger" rapamycin concentration, the rapamycin concentration would need to decrease by an order of magnitude for the system to revert to the OFF state, indicating that minor stochastic fluctuations in concentration will not affect results. As proteins are expressed and characterized in the proposed experimental plan, the kinetic parameters in the preliminary models will be updated to reflect the values measured in vitro, allowing for computationally driven experimental design of a bistable detection system.

Approach

Specific Aim 1: Investigate the In Vitro Use of Split Adenylate Cyclase for Small Molecule Detection.

Rational:

Split adenylate cyclase fusions have been extensively used to detect protein-protein interactions in vivo.[5,12,26] The inventors propose to fuse halves of split adenylate cyclase to analyte binding motifs for use as an in vitro detection scheme, which to their knowledge has never been attempted. Proof of concept demonstration may be performed by detecting rapamycin, a small molecule, via the FKBP12-rapamycin-FRB complex, which has been well characterized.[11] Split halves of adenylate cyclase have been fused to the FKBP12 and FRB protein domains, such that in the presence of rapamycin, adenylate cyclase will reconstitute and generate cAMP molecules.[12,13,27,28] The interaction of rapamycin with the FKBP12 and FRB domains will serve as the initial analyte sensing mechanism that activates the overall detection system. Background/spurious cAMP synthesis activity can be tuned by the inclusion of phosphodiesterase (PDE). PDE degrades cAMP into inactive AMP.[21] Therefore, cAMP will only accumulate when cAMP generation reliably exceeds the rate of degradation by PDE. Therefore, the objective of this aim may be to demonstrate proof-of-principle for in vitro, tunable detection of the small molecule rapamycin via the reconstitution of split adenylate cyclase.

Preliminary Data:

To date, the inventors have cloned, expressed, and purified positive and negative control fusions with split adenylate cyclase. To measure the catalytic activity of reconstituted split adenylate cyclase,[22] the T25 and T18 domains of adenylate cyclase were fused to self-assembling leucine zipper coiled-coil protein domains' that bring together T25 and T18 (in this case without any analyte required). The use of a leucine zipper fused to the T25 and T18 protein domains has been used previously as a positive control measurement for split adenylate cyclase in vivo.[5,12,22,26] The inventors used a heterodimeric coiled-coil peptide design (peptide EI and peptide KI) to prevent T25 and T18 homodimerization.[30] T25 and T18 fragments without the coiled-coil zipper fusions were used as a negative control. The inventors demonstrated activity of the reconstituted positive control fusions comparable to that of whole adenylate cyclase by combining the positive control fusions and negative control fragments with an excess of ATP for 30 minutes at 37° C. and measured cAMP accumulation via a commercial cAMP ELISA following the reaction (FIG. 2). This may be a significant finding, as the in vitro activity of purified split adenylate cyclase fragments has not previously been demonstrated to the inventors' knowledge. Currently, the inventors are in the process of optimizing soluble expression of T18 fusions to improve yield.

Figure 3:
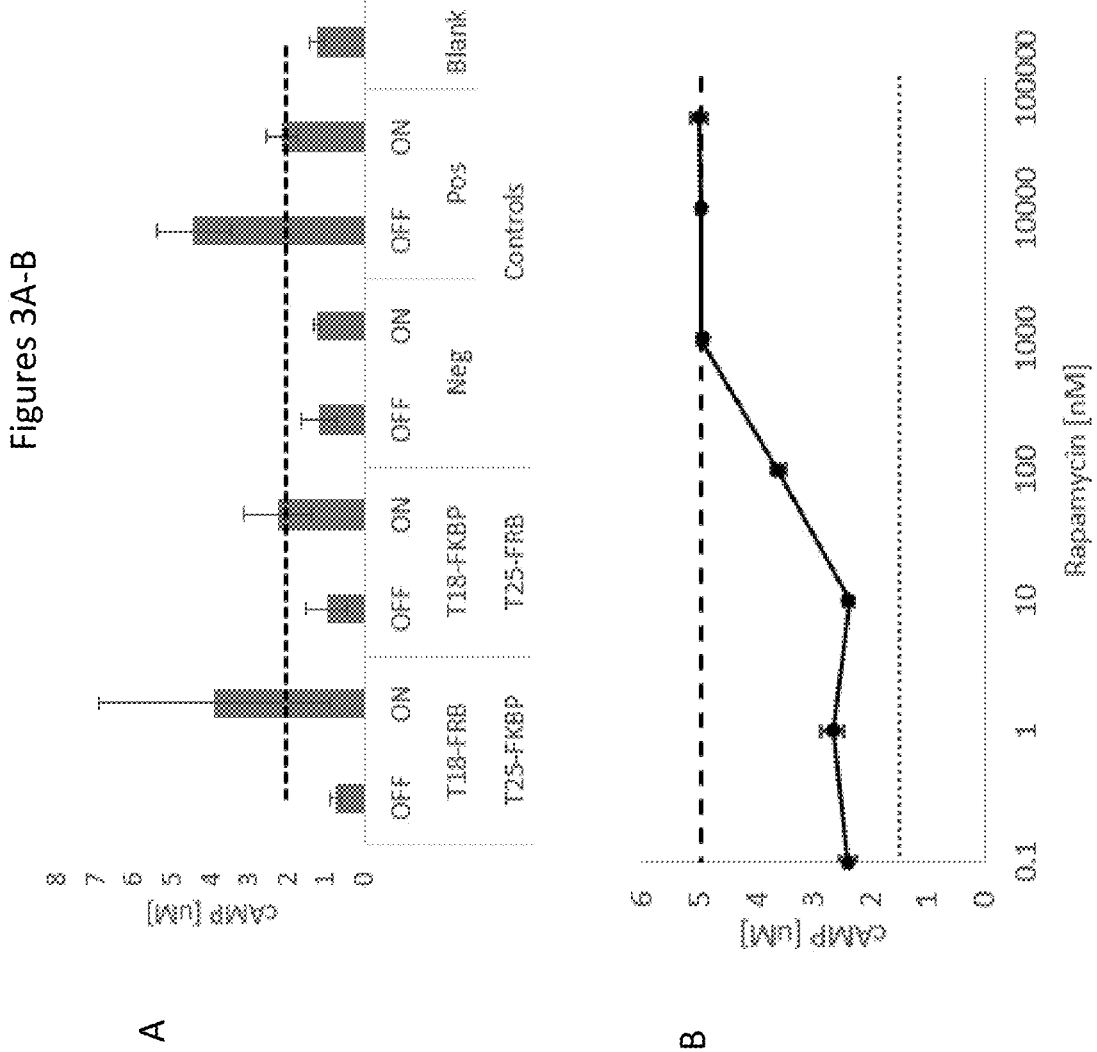
FIG. 3A-B show an example of the detection method's sensitivity using rapamycin as an analyte. (A) Activity of rapamycin sensing split adenylate cyclase fusions in the absence and presence of rapamycin (0 nm/OFF and 10000 nM/ON, respectively) compared to positive and negative controls. Rapamycin sensing protein fusions are composed of the split fragments of adenylate cyclase (T25 and T18) fused to the rapamycin binding domains FRB or FKBP12. The dashed line indicates the (+/−) cutoff as determined by the average of the negative controls+3 standard deviations. (B) Rapamycin sensing split adenylate cyclase fusions (T25-FRB and T18-FKBP) across a serial dilution of rapamycin concentrations (solid line) compared to the positive controls (dashed line) and blank (dotted line). All reactions were run in triplicate for 30 minutes at 37° C. with 100 nM of each adenylate cyclase fragment and 10 mM ATP in a 25 mM Tris 150 mM NaCl reaction buffer before being measure using a cAMP ELISA.
Figure 4:
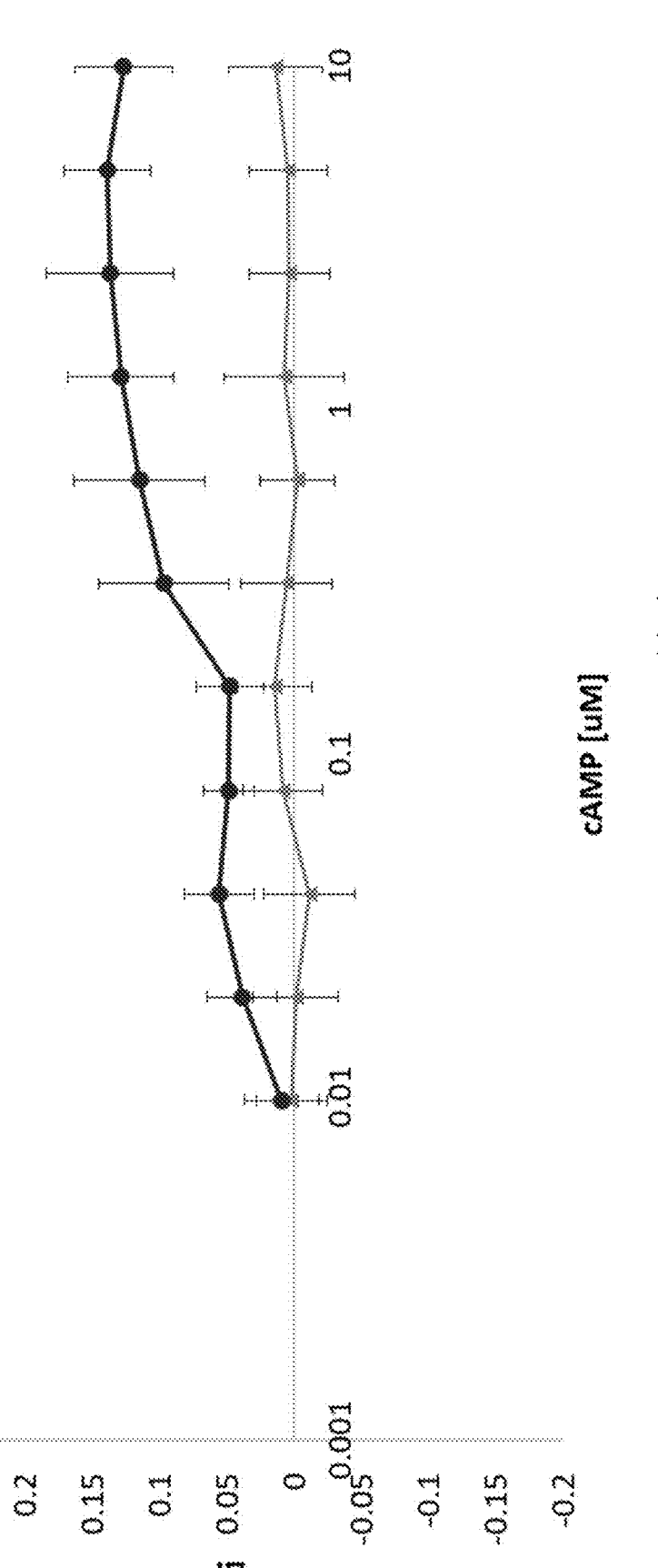
FIG. 4 shows change in fluorescence over a concentration range of cAMP using an embodiment of the detection method. Activity of an exemplary cAMP biosensor design over a serial dilution of cAMP concentrations, showing sensing of cAMP between 0.1 and 0.2 μM cAMP. The cAMP biosensor is composed of the cyclic nucleotide binding domain of the MlotiK1 potassium channel from *Mesorhizo-bium loti* (m1CNBD) with cyan fluorescent protein (CFP) fused to the C-terminus and yellow fluorescent protein (YFP) fused to the N-terminus. All reactions were run in triplicate for with 0.1 μM biosensor with 0.5 mg/mL BSA in a 25 mM Tris 150 mM NaCl reaction buffer. Fluorescence was measured immediately following the addition of cAMP with an excitation wavelength of 430 nm and emission wavelengths measured at 475 nm (CFP emission) and 529 nm (YFP FRET emission). The ratio of CFP/YFP emissions was used to measure change in fluorescence output, and the results are presented as the change in fluorescence ($\Delta F$) from the cAMP=0 μM condition.

The inventors have also constructed and tested rapamycin sensing proteins with T25 and T18 fragments fused with the FRB and FKBP12 rapamycin binding domains, respectively. When these fusions were mixed with a serial dilution of rapamycin, the system transitioned from an OFF state to an ON state between rapamycin concentrations of 10 and 100 nM (FIG. 3A). The inventors believe that with further optimization of system components, they can shift this detection limit as low as 500 pM, limited by the $K_d$ of the FRB-rapaymcin-FKBP12 complex.

Experimental Design:

Experiment 1.1. Determine cAMP accumulation kinetics of split adenylate cyclase with PDE and matrix effects. The behavior of split adenylate cyclase is well understood in vivo; however, to understand the results of reconstituted adenylate cyclase in the proposed system, a full understanding of the kinetic activity of split adenylate cyclase in vitro may be important. Here the inventors will focus on the cAMP synthesis rate with varying amounts of split adenylate cyclase and PDE. A serial dilution of split adenylate cyclase positive and negative control fusions (described above) over several orders of magnitude will be prepared in solution with excess ATP levels. cAMP generation by the positive and negative controls will be measured using commercially available cAMP ELISA kits. To test the effects of PDE, the inventors will use a serial dilution of commercially available PDE at select concentrations of split adenylate cyclase positive control. Expected results will show an accumulation of cAMP in solutions containing low PDE concentrations with high adenylate cyclase positive control concentrations, while solutions with high PDE concentration and low adenylate cyclase concentration (or the negative controls) will not accumulate cAMP. These measurements will be carried out in a variety of background environments, including the presence and absence of calmodulin (a known activator of adenylate cyclase, increasing catalytic activity several orders of magnitude[22,31] and common biological sample matrices (i.e., serum, urine, saliva). This series of measurements will give necessary information on catalytic activity of split adenylate cyclase in vitro that will guide experimental design of the rapamycin sensor described next.

Experiment 1.2. Rapamycin sensing using split adenylate cyclase. The T25 and T18 domains of adenylate cyclase fused to the FRB and FKBP12 protein domains will be tested for optimized rapamycin sensing. Adenylate cyclase activity will be measured by assessing cAMP accumulation over a range of rapamycin concentrations under a variety of conditions: a serial dilution of component protein fusions, a serial dilution of PDE, and the presence and absence of calmodulin. All measurements will be performed with in excess ATP.

Expected outcomes and alternative strategies: The inventors expect that steady state cAMP synthesis will increase linearly with adenylate cyclase in the presence of PDE. Turnover rates of adenylate cyclase on the order of 10/sec are anticipated, based on previous studies.[22] Human sample matrices may contain adenylate cyclase, cAMP, PDE or inhibitors and may cause variability in accumulation rates. This can be addressed by: (a) adding drugs that selectively inhibit eukaryotic adenylate cyclase or PDE and not the bacterial adenylate cyclase/PDE the inventors are using or (b) using an alternative enzyme system, such as protein kinase/phosphatase[32] or ppGpp bacterial alarmone systems,[33] both of which have similar dynamics to the proposed adenylate cyclase system.

Specific Aim 2: Investigate the Use of Split Adenylate Cyclase and cAMP Receptor Protein to Create an Autocatalytic Feedback Loop In Vitro.

Rational:

Auto-catalytic positive feedback protein circuits are a well characterized protein signaling network motif that have been previously shown to give rise to ultrasensitive responses in vivo.[4] The inventors propose to develop an in vitro auto-catalytic feedback loop based on the reconstitution of split adenylate cyclase driven by cAMP generation, which in turn synthesizes more cAMP. As shown in FIG. 1B, an initial concentration of cAMP produced from the Split Protein Sensor (FIG. 1A) will cooperatively bind to CRP fused with split adenylate cyclase halves. The binding of cAMP to CRP causes a conformational change in CRP, allowing it to bind to DNA fragments containing the CRP promoter sequence.[34-36] When multiple CRP binding sites are on the DNA, multiple CRP fusions will bind, allowing adenylate cyclase to reconstitute and generate more cAMP, driving further adenylate cyclase reconstitution. This feedback will continue until all the CRP fusions in the system are DNA-bound. Further, the cooperative binding of two cAMP molecules to CRP may fulfill a key mathematical requirement for the generation of bistable systems (a system that can only exist in a high or low state and jumps in between the two),[32] which have ideal properties for our diagnostic platform. Because of this bistable nature of the system, fluctuations in cAMP concentration after activation will not result in the returning to an OFF state. The objective of this aim may be to demonstrate bistable behavior of CRP-adenylate cyclase fragment fusions incorporated into an autocatalytic feedback loop.

Preliminary Data:

Modeled simulations of reconstituted adenylate cyclase across a range of PDE concentrations and initial "triggering" adenylate cyclase concentrations show tunable ON/OFF system behavior. The simulations showed that the system will rapidly turn to the ON state (i.e., all split adenylate cyclase fusions will be reconstituted by CRP binding to DNA fragments) when the rate of cAMP production by triggering adenylate cyclase exceeded the rate of degradation by PDE. The concentration of initial adenylate cyclase required to turn the system to the ON state could be tuned by changing the PDE concentration in the system.

Initial designs for the expression of the T25 and T18 halves of adenylate cyclase fused to E. coli CRP and Synechocystis sp. PCC 6803 SyCRP1 (a different species of CRP that will prevent off target dimerization of fusion populations[23] have been created. The inventors are currently in the process of expressing and purifying these protein fusions for characterization and validation.

Another embodiment may be using both halves of adenylate cyclase (T18 and T25) fused to a single chain homodimer for CRP (scCRP2). As such, the constructs may include or consist of (from N- to C-terminus) a split half of adenylate cyclase, a short linker, one CRP monomer, a long flexible linker, a second CRP monomer, and a His tag, which may be used for purification.

Experimental Design:

Experiment 2.1. Verification of feedback behavior. The T25 and T18 domains of adenylate cyclase will be fused to the CRP and SyCRP1. Small DNA fragments will be commercially synthesized including multiple copies of the consensus CRP promoter sequence[35] to act as a binding scaffold for the CRP fusions. The inventors will optimize the separation distance between promoter sequences on the fragments to ensure the CRP fusions bind on the same side of the DNA; synthesized fragments with promoter sequence separation distances ranging from 1 to 10 base pairs will be investigated. Reconstituted adenylate cyclase activity will be measured by assessing cAMP accumulation under a variety of conditions: scaffold DNA with varied promoter sequence separation lengths, a serial dilution of scaffold DNA concentrations, a serial dilution of component protein fusions, a serial dilution of PDE, and the presence and absence of calmodulin. All measurements will be performed with excess ATP. The assays will be triggered using a serial dilution of cAMP to initiate the feedback loop.

Expected outcomes and alternative strategies: The inventors expect that steady state cAMP concentrations will increase exponentially with initial cAMP concentration in the presence of PDE; additionally, the inventors expect the cAMP to reach steady state more rapidly than in the rapamycin sensing platform. Finally, the inventors expect the dose response curve to show hysteresis, indicating bistability in the feedback loop motif. A potential challenge is either (a) no amount of added cAMP will activate amplification, (b) spontaneous amplification happens without addition of cAMP, or (c) exponential amplification is not seen. A mathematical model of the system has been previously developed and will be used to identify the right balance of different components to achieve the desired bistable behavior.

Specific Aim 3: Incorporate a Fluorescent cAMP Biosensor to Interface with a Point-of-Care Reader.

Rational:

cAMP biosensors have been extensively used in vivo to evaluate in real-time the cAMP dynamics associated with cell signaling and motility.[9,37-40] These systems largely rely on FRET (Forster Resonance Energy Transfer), in which two fluorophores are fused to a single protein domain. When the protein is in a confirmation that brings the fluorophores in proximity, one fluorophore (the donor, ECFP in FIG. 1C) is excited and its emission wavelength is absorbed by the second fluorophore (the acceptor, EYFP in FIG. 1C) to excite it. When the conformation causes the fluorophores to move farther apart, the emission of the acceptor fluorophore will be decreased, causing a characteristic shift in the emission spectra.[41,42] The inventors will incorporate a previously characterized FRET-based cAMP biosensor for the in vitro detection of cAMP accumulation into the rapamycin sensing platform.[8,10] A hand-held fluorescent reader will be developed for the POC measurement of the detection system. The objective of this aim may be to demonstrate that the in vitro implementation of protein signaling networks can result in ultrasensitive, bistable detection of small molecules at the POC.

Preliminary Data:

Recently, the use of FRET-based cAMP biosensors has been demonstrated in vitro. Gruteser et al. modified the Epac1-cAMPs sensor[43] previously developed for in vivo use in order to express and purify the sensor from *E. coli* BL21(DE3) strains. This cAMP biosensor is composed of the Epac1 cAMP binding domain fused with Cyan Fluorescent Protein (ECFP, donor) and Yellow Fluorescent Protein (EYFP, acceptor). This sensor achieved cAMP detection at concentrations as low as 0.15 pmol (1.3 μM).[8] Mukherjee et al. developed an in vitro cAMP biosensor by fusing the cyclic nucleotide binding domain (CNDB) of the bacterial MlotiK1 channel with mCerulean (donor) and mCitrine (acceptor). This biosensor demonstrated improved sensitivity for cAMP in solution, with detection in the nanomolar range and a cAMP response time on the millisecond scale. This biosensor was also able to be desiccated and rehydrated with sample buffer while retaining activity, an important consideration for POC diagnostics.[10]

Experimental Design:

Experiment 3.1. FRET-based cAMP biosensor design and validation. cAMP biosensors will be constructed using both the Epac1[8] and m1CNDB[10] binding domains with EYFP and ECFP fused to the C- and N-termini. Fusion linkers will be investigated for optimal biosensor performance over a range of cAMP concentrations. cAMP biosensor response dynamics will be measured over a range of cAMP concentrations (aM to mM) in a variety of background environments, including common biological sample matrices (i.e., serum, urine, saliva). The biosensor will also be tested in environments where cAMP is being generated by split adenylate cyclase positive control fusions (Experiment 1.1).

Experiment 3.2. Experimental implementation of bistable rapamycin sensing with a POC reader. Based on ODE-model simulations, the inventors will set up mixtures of component proteins for rapamycin threshold detection. Specifically, the inventors will evaluate: (a) in the absence of activating rapamycin, how long is the mixture stably off? (b) in the presence of increasing amounts of activating rapamycin, is there a critical switching concentration to activate the system that matches the simulated results? (c) how long does it take the assay to develop at different concentrations of component proteins and activating rapamycin? and (d) can the critical switching concentration be shifted by changes in concentrations of component proteins as predicted by the model? These conditions will be initially validated using fluorescence measurement on a plate reader, before moving to fluorescence detection via a handheld fluorescence reader, exciting the biosensor FRET-donor fluorophore at 434 nm and measuring both fluorophore emission lines at 474 and 525 nm. POC FRET readers have been previously demonstrated using smartphone detection.[44]

Specific Aim 4: Incorporation of Binding Domains for Detection of Clinically Relevant Biomarker Targets.

Rational:

By nature of the design of the proposed platform, binding domains should act as a "plug-and-play" motif to detect a wide range of biomarker targets with known binding domains. After validating the system's ability to detect the small molecule rapamycin, the inventors will modify the biomarker sensing motif to detect the presence of a clinically relevant biomarker: Hepatitis C Core Antigen.

It is estimated that half of Americans infected with Hepatitis C Virus (HCV) are unaware of their infection status.[45] Left untreated, hepatitis infection can lead to cirrhosis and hepatocellular carcinoma, and it is estimated that viral hepatitis was responsible for 1.34 million deaths in 2015.[46] Current diagnostic methods for HCV rely on anti-HCV testing, which is not able to distinguish current from past infections. In the presence of a positive anti-HCV test, additional testing for HCV RNA must be performed to confirm an active infection. Methods to perform RNA detection are not readily available at the POC, due to high infrastructure and personnel requirements; as such, methods to determine active HCV at the POC are lacking. Detection of HCV core antigen (HCVcAg) offers an alternative cost effective method to confirm HCV infection at the POC.[47,48] Current methods to detect the HCVcAg require laboratory equipment such as the Abbott Architect device,[49] the proposed detection scheme would allow screening for active HCV to be performed at the bedside and away from large laboratory infrastructure. The objective of this aim may be to demonstrate the proposed platform's ability to detect additional clinically relevant biomarkers at diagnostically appropriate concentrations.

Experimental Design:

Experiment 4.1 HCVcAg sensing using split adenylate cyclase. The T25 and T18 domains of adenylate cyclase fused to hepatitis C binding domains[50-52] will be tested for sensing of HCVcAg. Adenylate cyclase activity will be measured by assessing cAMP accumulation via the FRET biosensor-based fluorescence shift over a range of HCVcAg concentrations under a variety of conditions: a serial dilution of component protein fusions, a serial dilution of PDE, and the presence and absence of calmodulin. All measurements will be performed with in excess ATP concentrations. Detection will also be performed with a variety of background buffer conditions, including serum and plasma as would be expected in clinical samples.

Expected outcomes and alternative strategies: The inventors expect the system will behave the same (bistable, sensitive sensing of an analyte), regardless of the binding domain in the sensing motif, and will therefore act as a "plug-and-play" platform for analyte sensing. The inventors expect sensing performance will be limited only by binding affinity for the analyte. If the inventors are unable to identify acceptable binders for HCVcAg with strong enough affinities, there are other potential clinical targets that would benefit from ultrasensitive protein detection at the point-of-care, including the ultrasensitive detection of pfHRP2 for the diagnosis of submicroscopic malaria in asymptomatic individuals necessary for eradication efforts[53] or the detection of SARS-CoV-2 Antigen for rapid, sensitive testing for population disease screening, for which multiple binders with high affinity have previously been demonstrated.[16]

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

CITED REFERENCES

1 Vashist S K. Point-of-Care Diagnostics: Recent Advances and Trends. *Biosensors.* 2017; 7:62. doi:10.3390/bios7040062, PMCID: PMC5746785

2. Koczula K M, Gallotta A. Lateral flow assays. *Essays Biochem.* 2016; 60:111-120. doi:10.1042/EBC20150012, PMCID: PMC4986465

3. Zhang Q, Bhattacharya S, Andersen M E. Ultrasensitive response motifs: basic amplifiers in molecular signalling networks. *Open Biol.* 2013; 3(4):130031-130031. doi:10.1098/rsob.130031, PMCID: PMC3718334

4. Zhang Q, Bhattacharya S, Conolly R B, Iii H J C, Kaminski N E, Andersen M E. Molecular Signaling Network Motifs Provide a Mechanistic Basis for Cellular Threshold Responses. *Environ Health Perspect.* 2014; 122(12):1261-1270. doi:10.1289/ehp.1408244, PMCID: PMC4256703

5. Battesti A, Bouveret E. The bacterial two-hybrid system based on adenylate cyclase reconstitution in *Escherichia coli.* Methods. 2012; 58(4):325-334. doi:10.1016/j.ymeth.2012.07.018

6. Tiwari A, Balazsi G, Gennaro M L, Igoshin O A. The interplay of multiple feedback loops with post-translational kinetics results in bistability of mycobacterial stress response. *Phys Biol.* 2010; 7(3):036005. doi:10.1088/1478-3975/7/3/036005, PMCID: PMC3543150

7 Kuszak A J, Sunahara R K. *Adenylyl Cyclases.* Vol Volume 2.; 2010. doi:10.1016/B978-0-12-374145-5.00171-6

8. Gruteser N, Kohlhas V, Balfanz S, et al. Establishing a sensitive fluorescence-based quantification method for cyclic nucleotides. *BMC Biotechnol.* 2020; 20(1). doi:10.1186/s12896-020-00633-y, PMCID: PMC7450941

9. Mathiesen J M, Vedel L, Brauner-Osborne H. CAMP biosensors applied in molecular pharmacological studies of G protein-coupled receptors. In: *Methods in Enzymology.* Vol 522. Academic Press Inc.; 2013:191-207. doi:10.1016/B978-0-12-407865-9.00011-X 10. Mukherjee S, Jansen V, Jikeli J F, et al. A novel biosensor to study cAMP dynamics in cilia and flagella. *Elife.* 2016; 5(4):130-137. doi:10.7554/eLife.14052, PMCID: PMC4811770

11. Banaszynski L A, Liu C W, Wandless T J. Characterization of the FKBPRapamycin.FRB Ternary Complex. *J Am Chem Soc.* 2005; 127(13):4715-4721. doi:10.1021/ja043277y 12. Olson M G, Goldammer M, Gauliard E, Ladant D, Ouellette S P. A bacterial adenylate cyclase-based two-hybrid system compatible with Gateway® cloning. In: *Methods in Molecular Biology.* Vol 1794. Humana Press Inc.; 2018:75-96. doi:10.1007/978-1-4939-7871-7_6

13. Karimova G, Ullmann A, Ladant D. A bacterial two-hybrid system that exploits a cAMP signaling cascade in *Escherichia coli. Methods Enzymol.* 2000; 328:59-73. doi:10.1016/s0076-6879(00)28390-0

14. Cameron A D S, Redfield R J. CRP Binding and Transcription Activation at CRP-S Sites. *J Mol Biol.* 2008; 383(2):313-323. doi:10.1016/j.jmb.2008.08.027

15. Muyldermans S. Nanobodies: Natural Single-Domain Antibodies. *Annu Rev Biochem.* 2013; 82(1):775-797. doi:10.1146/annurev-biochem-063011-092449

16. Cao L, Goreshnik I, Coventry B, et al. De novo design of picomolar SARS-CoV-2 miniprotein inhibitors. *Science* (80-). 2020; 370(6515):426-431. doi:10.1126/science.abd9909, PMCID: PMC7857403

17. Sun Y S, Landry J P, Fei Y Y, et al. Effect of fluorescently labeling protein probes on kinetics of protein-ligand reactions. *Langmuir.* 2008; 24(23):13399-13405. doi:10.1021/1a802097z, PMCID: PMC2721158

18. Schoof M, Faust B, Saunders R A, et al. An ultrapotent synthetic nanobody neutralizes SARS-CoV-2 by stabilizing inactive Spike. *Science* (80-). 2021; 370(6523):1473-1479. doi:10.1126/science.abe3255, PMCID: PMC7857409

19. Marquart L, Butterworth A, McCarthy J S, Gatton M L. Modelling the dynamics of *Plasmodium falciparum* histidine-rich protein 2 in human malaria to better understand malaria rapid diagnostic test performance. *Malar* J. 2012; 11:74. doi:10.1186/1475-2875-11-74, PMCID: PMC3359291

20. Ladant D, Ullmann A. *Bordetella pertussis* adenylate cyclase: A toxin with multiple talents. *Trends Microbiol.* 1999; 7(4):172-176. doi:10.1016/50966-842X(99)01468-7

21. Adderley S P, Sprague R S, Stephenson A H, Hanson M S. Regulation of cAMP by phosphodiesterases in erythrocytes. *Pharmacol Reports.* 2010; 62(3):475-482. doi:10.1016/S1734-1140(10)70303-0, PMCID: PMC2922877

22. Karimova G, Pidoux J, Ullmann A, Ladant D. A bacterial two-hybrid system based on a reconstituted signal transduction pathway. *Proc Natl Acad Sci.* 1998; 95(10):5752-5756. doi:10.1073/pnas.95.10.5752, PMCID: PMC20451

23. Yoshimura H, Hisabori T, Yanagisawa S, Ohmori M. Identification and characterization of a novel cAMP receptor protein in the cyanobacterium *Synechocystis* sp. PCC 6803. *J Biol Chem.* 2000; 275(9):6241-6245. doi:10.1074/jbc.275.9.6241

24. Ranganathan S, Cheung J, Cassidy M, Ginter C, Pata J D, Mcdonough K A. Novel structural features drive DNA binding properties of Cmr, a CRP family protein in TB complex mycobacteria. *Nucleic Acids Res.* 2017; 46(1): 403-420. doi:10.1093/nar/gkx1148, PMCID: PMC5758884

25. Wang H, Yan Z, Yang S, Cai J, Robinson H, Ke H. Kinetic and structural studies of phosphodiesterase-8A and implication on the inhibitor selectivity. *Biochemistry.* 2008; 47(48):12760-12768. doi:10.1021/bi801487x, PMCID: PMC2646200

26. Ouellette S P, Karimova G, Davi M, Ladant D. Analysis of Membrane Protein Interactions with a Bacterial Adenylate Cyclase-Based Two-Hybrid (BACTH) Technique. *Curr Protoc Mol Biol.* 2017; 118(1). doi:10.1002/cpmb.36

27. Wehr M C, Rossner M J. Split protein biosensor assays in molecular pharmacological studies. *Drug Discov Today.* 2016; 21(3):415-429. doi:10.1016/j.drudis.2015.11.004

28. Stein V, Alexandrov K. Protease-based synthetic sensing and signal amplification. *Proc Natl Acad Sci.* 2014; 111 (45):15934-15939. doi:10.1073/pnas.1405220111, PMCID: PMC4234609

29. Edgell C L, Smith A J, Beesley J L, Savery N J, Woolfson D N. De Novo Designed Protein-Interaction Modules for In-Cell Applications. *ACS Synth Biol.* Published online Feb. 6, 2020:acssynbio.9b00453. doi:10.1021/acssynbio.9b00453

30. Aronsson C, Danmark S, Zhou F, et al. Self-sorting heterodimeric coiled coil peptides with defined and tuneable self-assembly properties. *Sci Rep.* 2015; 5(1):1-10. doi:10.1038/srep14063, PMCID: PMC4570195

31. Ladant D. Interaction of *Bordetella pertussis* adenylate cyclase with calmodulin. Identification of two separated calmodulin-binding domains. *J Biol Chem.* 1988; 263(6): 2612-2618.

32. Angeli D, Ferrell J E, Sontag E D. Detection of multistability, bifurcations, and hysteresis in a large class of biological positive-feedback systems. *Proc Natl Acad Sci.* 2004; 101(7):1822-1827. doi:10.1073/pnas.0308265100, PMCID: PMC357011

33. Dalebroux Z D, Swanson M S. PpGpp: Magic beyond RNA polymerase. *Nat Rev Microbiol.* 2012; 10(3):203-212. doi:10.1038/nrmicro2720

34. Lawson C L, Swigon D, Murakami K S, Darst S A, Berman H M, Ebright R H. Catabolite activator protein: DNA binding and transcription activation. *Curr Opin Struct Biol.* 2004; 14(1):10-20. doi:10.1016/j.sbi.2004.01.012, PMCID: PMC2765107

35. Ebright R H, Ebright Y W, Gunasekera A. Consensus DNA site for the *Escherichia coli* catabolite gene activator protein (CAP): CAP exhibits a 450-fold higher affinity for the consensus DNA site than for the *E. coli* lac DNA site. *Nucleic Acids Res.* 1989; 17(24):10295-10305. doi:10.1093/nar/17.24.10295, PMCID: PMC335301

36. Parkinson G, Wilson C, Gunasekera A, Ebright Y W, Ebright R E, Berman H M. Structure of the CAP-DNA complex at 2.5 A resolution: A complete picture of the protein-DNA interface. *J Mol Biol.* 1996; 260(3):395-408. doi:10.1006/jmbi.1996.0409

37. Vedel L, Brauner-Osborne H, Mathiesen J M. A cAMP biosensor-based high-throughput screening assay for identification of Gs-coupled GPCR ligands and phosphodiesterase inhibitors. *J Biomol Screen.* 2015; 20(7): 849-857. doi:10.1177/1087057115580019

38. Hackley C R, Mazzoni E O, Blau J. CAMPr: A Single-Wavelength Fluorescent Sensor for Cyclic AMP. *Sci Sig-*

*nal.* 2018; 11(520): eaah3738. doi: 10.1126/scisignal. aah3738, PMCID: PMC5863242

39. Klarenbeek J, Goedhart J, van Batenburg A, Groenewald D, Jalink K. Fourth-Generation Epac-Based FRET Sensors for cAMP Feature Exceptional Brightness, Photostability and Dynamic Range: Characterization of Dedicated Sensors for FLIM, for Ratiometry and with High Affinity. Anderson K I, ed. *PLoS One.* 2015; 10(4):e0122513. doi:10.1371/journal.pone.0122513, PMCID: PMC4397040

40. Dipilato L M, Zhang J. The role of membrane microdomains in shaping β 2-adrenergic receptor-mediated cAMP dynamics. *Mol Biosyst.* 2009; 5(8):832-837. doi: 10.1039/b823243a 41. Chen T, He B, Tao J, et al. Application of Förster Resonance Energy Transfer (FRET) technique to elucidate intracellular and In Vivo biofate of nanomedicines. *Adv Drug Deliv Rev.* 2019; 143:177-205. doi:10.1016/j.addr.2019.04.009

42. Kaminski C F, Rees E J, Schierle G S K. A quantitative protocol for intensity-based live cell FRET imaging. *Methods Mol Biol.* 2014; 1076:445-454. doi:10.1007/978-1-62703-649-8_19

43. Nikolaev V O, Bilnemann M, Hein L, Hannawacker A, Lohse M J. Novel single chain cAMP sensors for receptor-induced signal propagation. *J Biol Chem.* 2004; 279 (36):37215-37218. doi:10.1074/jbc.C400302200

44. Petryayeva E, Algar W R. Single-step bioassays in serum and whole blood with a smartphone, quantum dots and paper-in-PDMS chips. *Analyst.* 2015; 140(12):4037-4045. doi:10.1039/c5an00475f 45. CDC. *Hepatitis C Kills More Americans than Any Other Infectious Disease|CDC Online Newsroom|CDC.*; 2014. Accessed Oct. 5, 2018. https://www.cdc.gov/media/releases/2016/p0504-hepc-mortality.html 46. WHO. *Global Hepatitis Report,* 2017.; 2017. Accessed Oct. 5, 2018. http://apps.who.int/iris/bitstream/handle/10665/255016/9789241565455-eng.pdf;j sessionid= DF4D912B1D86DDO1DB8CB54F148DB5E7?sequence=1

47. Cresswell F V, Fisher M, Hughes D J, Shaw S G, Homer G, Hassan-Ibrahim M O. Hepatitis C Core Antigen Testing: A Reliable, Quick, and Potentially Cost-effective Alternative to Hepatitis C Polymerase Chain Reaction in Diagnosing Acute Hepatitis C Virus Infection. *Clin Infect Dis.* 2015; 60(2):263-266. doi:10.1093/cid/ciu782

48. Tillmann H L. Hepatitis C virus core antigen testing: Role in diagnosis, disease monitoring and treatment Hans L Tillmann. *World J Gastroenterol.* 2014; 20(22):6701-6706. doi:10.3748/wjg.v20.i22.6701, PMCID: PMC4051911

49. Morota K, Fujinami R, Kinukawa H, et al. A new sensitive and automated chemiluminescent microparticle immunoassay for quantitative determination of hepatitis C virus core antigen. *J Virol Methods.* 2009; 157(1):8-14. doi:10.1016/j.jviromet.2008.12.009

50. Aoyagi K, Ohue C, Iida K, et al. Development of a simple and highly sensitive enzyme immunoassay for hepatitis C virus core antigen. *J Clin Microbiol.* 1999; 37(6):1802-1808. doi:10.1128/jcm.37.6.1802-1808.1999, PMCID: PMC84955

51. Tanaka E, Ohue C, Aoyagi K, et al. Evaluation of a new enzyme immunoassay for hepatitis C virus (HCV) core antigen with clinical sensitivity approximating that of genomic amplification of HCV RNA. *Hepatology.* 2000; 32(2):388-393. doi:10.1053/jhep.2000.9112

52. Takahashi K, Okamoto H, Kishimoto S, et al. Demonstration of a hepatitis C virus-specific antigen predicted from the putative core gene in the circulation of infected hosts. *J Gen Virol*. 1992; 73(3):667-672. doi:10.1099/0022-1317-73-3-667

53. Grant B D, Smith C A, Karvonen K, Richards-Kortum R. Highly Sensitive Two-Dimensional Paper Network Incorporating Biotin-Streptavidin for the Detection of Malaria. *Anal Chem*. 2016; 88(5):2553-2557. doi: 10.1021/acs.analchem.5b03999, PMCID: PMC5523814

What is claimed is:

1. A method of detecting an analyte comprising:
adding to a sample comprising adenosine triphosphate and an unknown concentration of analyte detection reagents comprising a first reagent and a second reagent, the first reagent comprises a first protein bound to a first fragment of a first CAMP catalyzing enzyme; the second reagent comprises a second protein bound to a second fragment of the first CAMP catalyzing enzyme, the first protein and the second protein are configured to form with the analyte a protein-analyte-protein complex, the first fragment of the first CAMP catalyzing enzyme and the second fragment of the first cAMP catalyzing enzyme together restitute the full first CAMP catalyzing enzyme; and
then measuring a cAMP concentration in the sample and determining the concentration of the analyte from the measured cAMP concentration, wherein the analyte is rapamycin, one of the first protein and the second protein is FKBP12-rapamycin-binding (FRB) protein and the other of the first protein and the second protein is FK506 (Tacrolimus)-Binding Protein 12 (FKBP12).

2. The method of claim 1, wherein the first CAMP catalyzing enzyme is adenylate cyclase.

3. The method of claim 2, wherein one of the first fragment of the first CAMP catalyzing enzyme and the second fragment of the first CAMP catalyzing enzyme is a T25 fragment of the adenylate cyclase and the other of the first fragment of the first CAMP catalyzing enzyme and the second fragment of the first CAMP catalyzing enzyme is a T18 fragment of the adenylate cyclase.

4. The method of claim 1, wherein the measuring the cAMP concentration in the sample comprises:
adding to the sample a fusion protein comprising a donor fluorophore, an acceptor fluorophore and a cyclic nucleotide binging domain (CNBD) that binds CAMP and
measuring an emission spectrum of the sample excited at an excitation wavelength of the donor fluorophore, wherein the donor fluorophore and the acceptor fluorophore form a complex with CAMP via the cyclic nucleotide binding domain and wherein an emission wavelength of the donor fluorophore overlaps with an excitation length of the acceptor fluorophore.

5. The method of claim 4, wherein the donor fluorophore is Enhanced Cyan Fluorescent Protein (ECFP) and the acceptor fluorophore is Enhanced Yellow Fluorescent Protein (EYFP).

6. The method of claim 1, wherein the determining the concentration of the analyte comprises determining that the concentration of the analyte is above an analyte threshold concentration for the measured cAMP concentration being above a cAMP threshold concentration.

7. The method of claim 6, wherein the detection reagents further comprise a sixth reagent, which is a CAMP deactivator, wherein a concentration of the sixth reagent selects a value of the CAMP threshold concentration and a value of the analyte threshold concentration.

8. The method of claim 7, wherein the CAMP deactivator is phosphodiesterase.

9. A kit for determining a concentration of an analyte, comprising a first reagent comprises a first protein bound to a first fragment of a first CAMP catalyzing enzyme; and
a second reagent comprises a second protein bound to a second fragment of the first CAMP catalyzing enzyme, the first protein and the second protein are configured to form with the analyte a protein-analyte-protein complex, the first fragment of the first CAMP catalyzing enzyme and the second fragment of the first CAMP catalyzing enzyme together restitute the full first CAMP catalyzing enzyme, wherein the analyte is rapamycin, one of the first protein and the second protein is FKBP12-rapamycin-binding (FRB) protein and the other of the first protein and the second protein is FK506 (Tacrolimus)-Binding Protein 12 (FKBP12).

10. The kit of claim 9, wherein the first CAMP catalyzing enzyme is adenylate cyclase.

11. The kit of claim 10, wherein one of the first fragment of the first CAMP catalyzing enzyme and the second fragment of the first CAMP catalyzing enzyme is a T25 fragment of the adenylate cyclase and the other of the first fragment of the first CAMP catalyzing enzyme and the second fragment of the first CAMP catalyzing enzyme is a T18 fragment of the adenylate cyclase.

12. The kit of claim 9, wherein the first reagent comprises FKBP12 protein bound to a T25 fragment of adenylate cyclase; and the second reagent comprises FRB protein bound to a T18 fragment of the adenylate cyclase.

13. The kit of claim 9, wherein the first reagent comprises FRB protein bound to a T25 fragment of adenylate cyclase; and the second reagent comprises FKBP12 protein bound to a T18 fragment of the adenylate cyclase.

14. The kit of claim 9, wherein further comprising a fusion protein comprising a donor fluorophore, an acceptor fluorophore and a cyclic nucleotide binding domain (CNBD) that binds cAMP, wherein the donor fluorophore and the acceptor fluorophore form a complex with CAMP via the cyclic nucleotide binding domain and wherein an emission wavelength of the donor fluorophore overlaps with an excitation wavelength of the acceptor fluorophore.

15. The kit of claim 14, wherein the donor fluorophore is ECFP and the acceptor fluorophore is EYFP.

16. The kit of claim 9, further comprising a sixth reagent, which is a cAMP deactivator, wherein a concentration of the sixth reagent defines a value of a threshold concentration for the analyte.

17. The kit of claim 16, wherein the CAMP deactivator is phosphodiesterase.

18. The kit of claim 16, wherein the value of the threshold concentration for the analyze is within a range from 100 pM to 500 nM.

* * * * *